United States Patent [19]

Stucks

[11] Patent Number: 5,062,416
[45] Date of Patent: Nov. 5, 1991

[54] PENILE ERECTION SYSTEM

[76] Inventor: Albert A. Stucks, 6202 Spencer Hwy., #11, Pasadena, Tex. 77505

[21] Appl. No.: 278,489

[22] Filed: Dec. 1, 1988

[51] Int. Cl.$^5$ ............................................. A61F 2/26
[52] U.S. Cl. ..................................................... 128/79
[58] Field of Search .......................................... 128/79

[56] References Cited

U.S. PATENT DOCUMENTS

| | | | |
|---|---|---|---|
| 3,954,102 | 5/1976 | Buuck | 128/79 |
| 4,235,227 | 11/1980 | Yamanaka | 128/79 |
| 4,407,278 | 10/1983 | Burton et al. | 128/79 |
| 4,566,446 | 1/1986 | Fogarty | 128/79 |
| 4,782,826 | 11/1988 | Fogarty | 128/79 |

Primary Examiner—Cary E. Stone
Attorney, Agent, or Firm—Kenneth D. Baugh

[57] ABSTRACT

The invention relates to an improved erection system (30) for implanting in a male (10). The erection system (30) includes first and second inflatable cylinders (32) and (34) for positioning within first and second corpora cavernosa regions (24) of the male's penis (16). A first valve (48) is mounted in the first cylinder (32) to direct and maintain fluid in the first cyclinder and release fluid therefrom. A secon valve (48) is mounted in the second cylinder (34) to direct and maintain fluid in the second cylinder and release fluid therefrom. A pump (40) is provided to pump fluid from a reservoir (38) to the first and second valves (48) to inflate the first and second cylinders (32) and (34) and cause an erection of the male's penis (16) when the valves (48) are opened. After sufficient fluid (48) is pumped into the cylinders (32) and (34) the erection is maintained by closing the valves (48). The penis (16) can thereafter be relaxed by again opening the valves (48).

3 Claims, 3 Drawing Sheets

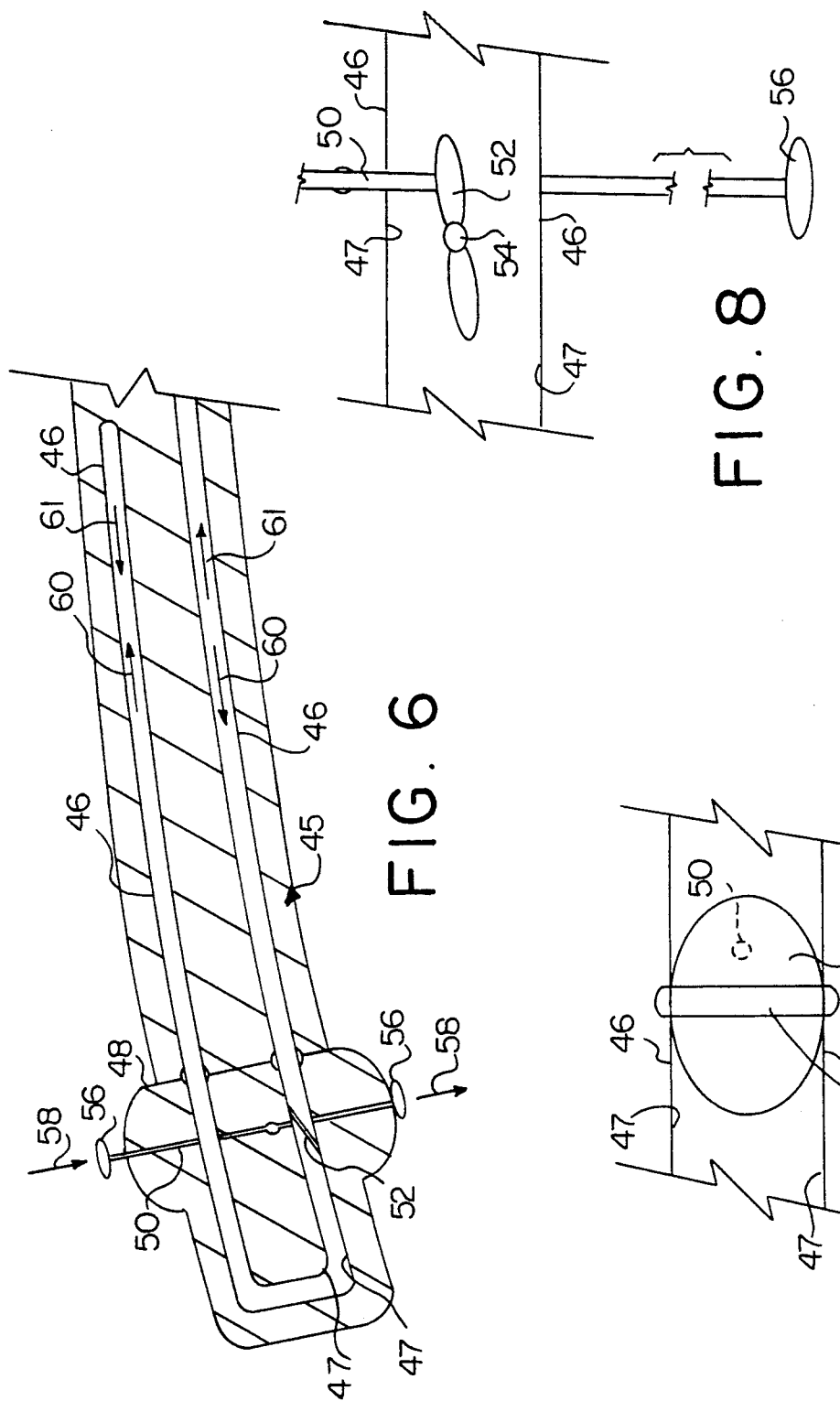

PENILE ERECTION SYSTEM

TECHNICAL FIELD

This invention relates to an apparatus to combat impotency and more particularly to an improved penile erection system. Impotence is a flustrating condition in which a man can't get an erection or keep it long enough for sexual intercourse. Most men occasionally experience erection problems. But for one in ten, impotence becomes a chronic condition. Erection problems can be caused by illnesses, drugs, depression, or a vicious cycle of stress and anxiety. Whatever the cause erection problems can undermine a man's self confidence and erode his relationship with his partner. In some cases this condition can be remedied by conventional therapy. However in those instances where therapy does not work implantable penile erection systems have become the desirable remedy for impotence.

BACKGROUND ART

A number of attempts have been made to provide penile erection systems for remedying impotence. One of the more common penile erection systems is an inflatable system. This system includes a pair of inflatable tubes implanted in the corpora cavernosa of the penis. Each of the tubes is connected to a reservoir of inflating fluid which is also implanted elsewhere in the body. Although this system works the implantation of tubes in the penis restricts the blood flow throughout the penis. As a result excess fluid in the penis not recirculated through the reservoir may become cold thus causing frontal portions of the penis to be cold or uncomfortable when erected.

DISCLOSURE OF THE INVENTION

The invention relates to an erection system for implanting in a male. The erection system in accordance with this invention includes first and second inflatable cylinders for positioning within first and second corpora cavernosa regions of the male's penis. A first fluid transfer means is mounted in the first cylinder to direct fluid into the first cylinder and maintain fluid therein. A second fluid transfer means is mounted in the second cylinder to direct fluid into the second cylinder and maintain fluid therein. A reservoir containing fluid is coupled to the first and second fluid transfer means. A pump is provided to pump fluid from the reservoir to the first and second fluid transfer means to inflate the first and second cylinders and cause an erection of the male penis when desired.

BRIEF DESCRIPTION OF THE DRAWING

The details of the invention will be described in connection with the accompanying drawing in which:

FIG. 6 is a cross sectional view taken along lines 6—6 of FIG. 4 illustrating the valve in accordance with the principles of the invention.

FIG. 7 is a side view of the valve arrangement illustrated in FIG. 6 in accordance with the principles of the invention.

FIG. 8 is a top view of the valve arrangement illustrated in FIG. 8 in accordance with the principles of the invention.

DESCRIPTION OF THE PREFERRED EMBODIMENT

Figure 1:
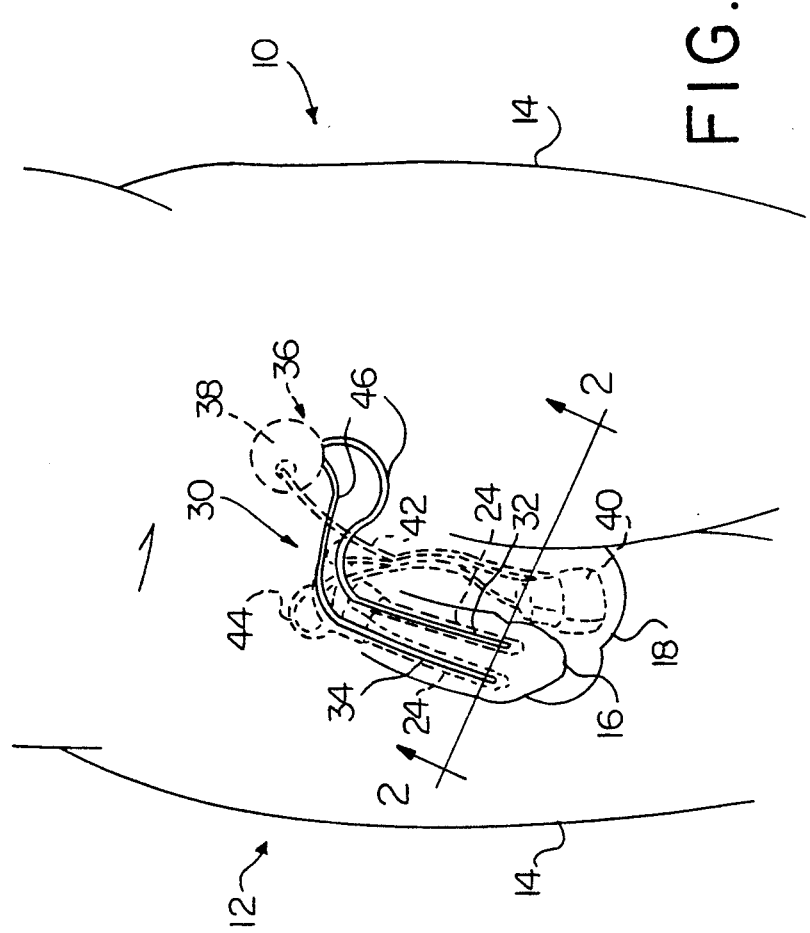
FIG. 1 is a front elevation view illustrating the trunk of a male showing the Improved Penile Erection System in accordance with the principles of this invention.
Figure 2:
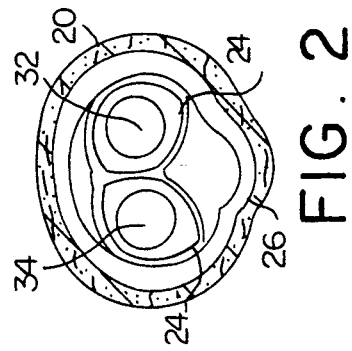
FIG. 2 is a cross sectional view taken along line 2—2 of FIG. 1 illustrating a penis equipped with cylinders that have been implanted in accordance with the principles of this invention.

Referring to FIG. 1 there is shown portions of a male 10 having a trunk generally designated by the numeral 12. The trunk is shown including the male's legs 14, a penis, generally designated by the numeral, 16 and a scrotum 18. As shown in FIG. 2 the penis 16 includes an outer layer of skin 20, tissue and blood vessels 22, interior portions 24 known as the copora cavernosa region and the corpora spongiosum 26. The copora cavernosa 24 is the region or chamber that normally fills with blood during an erection.

Figure 3:
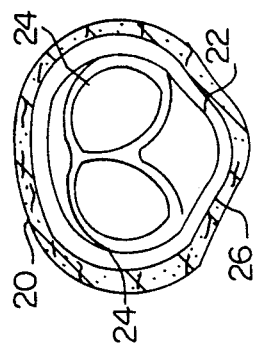
FIG. 3 is a cross sectional view corresponding to FIG. 2 illustrating a penis as it appears prior to implantation of the cylinders in accordance with the principles of the invention.

The male 10 is provided with a penile erection system, generally designated by the numeral, 30. Referring to FIGS. 1 as well as FIGS. 4 and 5 the penile erection system 30 includes a pair of expansible cylinders, generally designated by the numerals, 32 and 34. The cylinders 32 and 34 are mounted in spaced relationship in the collasped corpora cavernosa region 24 (FIG. 2) of the penis and are provided to the function as the corpora cavernosa (FIG. 3). Specifically, each cylinder 32 and 34 is expansible circumferentially and also longitudinally.

The penile erection system 30 is also provided with a reservoir, generally designated by the numeral, 36 containing a warm fluid 38 therein. The reservoir 36 can be placed on the male trunk 12 under the abdominal muscles. A pump 40 is provided and mounted in the scrotum 18. The pump 40 is provided to pressurize the fluid 38 in the reservoir 36 and cause fluid flow into the cylinders 32 and 34. The pump is coupled to the reservoir 36 by a tube 42 and to each cylinder 32 and 34 by a tube 44. The tube 44 allows the fluid to circulate from the cylinder back to the reservoir to the cylinder to raise the temperature of the penis back to normal.

The cylinders 32 and 34 are each provided with a fluid transfer member, generally designated by the numeral, 45 (FIG. 6). Each fluid transfer member 45 includes a tube 46, mounted in one of the cylinders 32 and 34 and coupled at one end thereof to receive fluid from the reservoir 38. Each fluid transfer member 45 also includes a check valve 48 which is coupled in the tube 46 at a front portion of the penis 16. The check valves 48 control the flow of fluid 38 into and out of the tubes 46 and thus the cylinders 32 and 34. The check valves 48, may be, for example, of a type illustrated in FIGS. 6 through 8. The valve 48 is shown including a shaft member 50 which is mounted for slidably movement on the cylinders 32 and 34 and a stem or shutter member 52. The stem 52 includes a shaft 54 which is coupled between wall portions 47 of the tube 46. The shaft 50 may also include raised portions 56 which may be coupled to its ends to facilatate movement of the shaft. The shaft 50 is coupled to the stem 52 so that upon pushing it in the direction of arrow 58 the stem will move clockwise thus opening the valve 48. This permits fluid to flow into or out of the tube 46 as illustrated by the arrows 60 and 61. When the shaft 50 is moved in the other direction this closes the valve 48 and maintaines fluid in the tube 46. The valve 48 can be manually opened by squeezing the penis in the area of the valve.

It should be understood that other valve constructions can be used without departing from the spirit and scope of the invention.

Figure 4:
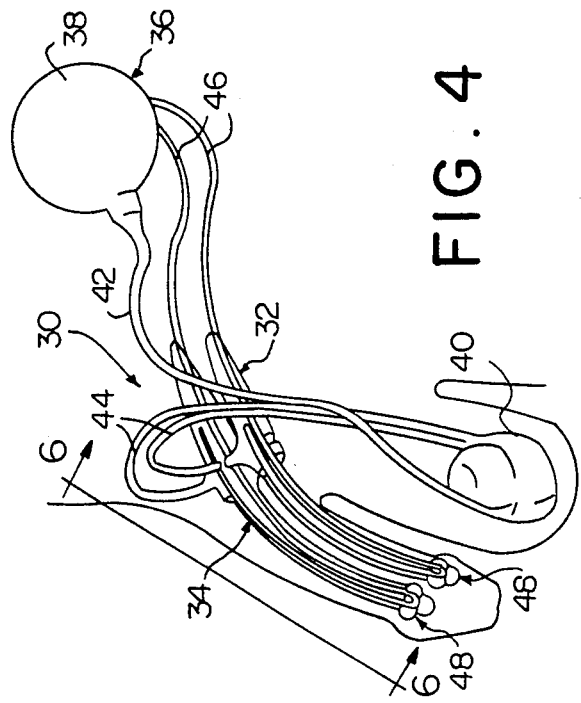
FIG. 4 is a side elevation view of the Improved Penile Erection System implanted in accordance with the principles of this invention.
Figure 5:
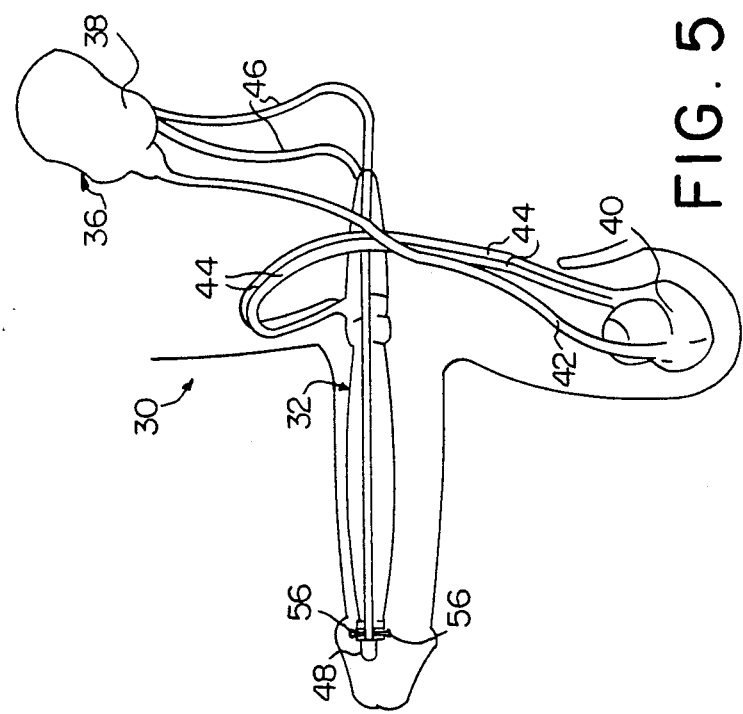
FIG. 5 is a side elevation view of the Improved Penile Erection System illustrating one cylinder in the inflated position in accordance with the principles of the invention.

When the penile erection system 30 is implanted and not in use the penis 18 is maintained in a normal relaxed condition as illustrated in FIG. 4. When the male wants an erection, he transfers fluid into the cylinders 32 and 34 from the reservoir 36 by squeezing the pump 40 while keeping the valves 48 open with the fingers. This allows circulation of fluid into the tubes 46. As a result fluid flows into the chambers 22 of the penis 18 that is normally filled with blood. While transferring the fluid to the cylinders the tubes 44 then allows the fluid to circulate from the cylinders 32 and 34 back to the pump 40. The fluid then circulates through tube 42 to reservoir 36 and back to the cylinders 32 and 34 through tubes 46. This recirculation of the fluid raises the temperature of the penis thereby warming the penis and causing an erection. Once the valves 48 are released the valves maintain the pressure in the cylinders 32 and 34 thus maintaining the erection. On the other hand when it is desired to conclude the erection the valves 48 are opened without activating the pump thus all the fluid returns through tubes 46 from the cylinders to the reservoir 36. As a result the penis 18 returns to its normal relaxed condition.

The invention has been shown and described in what is considered to be the most practical and preferred embodiment. However, it should be recognized that changes may be made by those skilled in the art without departing from the spirit and scope of the invention.

What is claimed:

1. An erection system for implanting in a male including:
   a first inflatable cylinder for positioning within a first corpora carvernosa region within the male's penis;
   a second inflatable cylinder for positioning within a second corpora carvernosa region within the male's penis;
   a first fluid transfer means mounted in the first cylinder for directing fluid into the first cylinder and maintaining the fluid therein in a first state and releasing the fluid therefrom in a second state;
   a second fluid transfer means mounted in the second cylinder for directing fluid into the second cylinder and maintaining the fluid therein in a first state and releasing the fluid therefrom in a second state;
   a reservoir having fluid therein which is coupled to the first and second transfer means;
   a pump for pumping fluid from the reservoir to the first and second fluid transfer means so that when fluid is maintained in the first and second fluid transfer means during the first state the first and second cylinders are inflated and so that when fluid is released from the first and second fluid transfer means during the second state the first and second cylinders are deflated; and
   a fluid circulating means for allowing the fluid to circulate from the first and second cylinders through the pump, and back to the reservoir while fluid is transferred to the cylinders and the cylinders are being inflated to the first state whereby the recirculation of the fluid warms the penis.

2. An erection system as defined in claim 1 wherein the first fluid transfer means includes;
   a first elongated tube member mounted in the first cylinder and coupled to the reservoir; and
   a first valve coupled in the tube member so that when the pump is activated the valve can be activated to allow fluid to flow into and maintained in the tube and so that when the pump is deactivated the valve can be activated to release all the fluid from the tube into the reservoir.

3. An erection system as defined in claim 2 wherein the second fluid transfer means includes;
   a second elongated tube member mounted in the second cylinder and coupled to the reservoir; and
   a second valve coupled in the tube member so that the valve can be activated to allow fluid to flow into and maintained in the tube and so that when the pump is deactivated the valve can be activated to release all the fluid from the tube into the reservoir.

* * * * *